United States Patent [19]

Wunder et al.

[11] 4,169,367

[45] Oct. 2, 1979

[54] DEVICE FOR TESTING OF CONTACT ACTION BETWEEN ROTATING AND STATIONARY STRUCTURAL ELEMENTS OF FLOW RELATED ENGINES, ESPECIALLY GAS TURBINE POWER PLANTS

[75] Inventors: Max Wunder; Albert Sickinger, both of Munich, Fed. Rep. of Germany

[73] Assignee: Motoren- und Turbinen-Union Munchen GmbH, Fed. Rep. of Germany

[21] Appl. No.: 886,760

[22] Filed: Mar. 15, 1978

[30] Foreign Application Priority Data

Mar. 15, 1977 [DE] Fed. Rep. of Germany ....... 2711176

[51] Int. Cl.² .................. G01N 3/56; G01M 13/00
[52] U.S. Cl. .............................................. 73/7; 73/9
[58] Field of Search .................. 73/7, 8, 9, 432 R

[56] References Cited

U.S. PATENT DOCUMENTS

| 2,010,049 | 8/1935 | Abbott, Jr. et al. | 73/8 |
|---|---|---|---|
| 2,519,556 | 8/1950 | Fish | 73/7 |
| 2,590,839 | 4/1952 | Clapham | 73/7 |
| 3,312,100 | 4/1967 | Ainslie | 73/7 |
| 3,444,720 | 5/1969 | Link | 73/9 |
| 3,899,917 | 8/1975 | Kisbany | 73/8 |
| 3,948,080 | 4/1976 | Boyd | 73/9 |

*Primary Examiner*—John Petrakes
*Attorney, Agent, or Firm*—Craig and Antonelli

[57] ABSTRACT

A device for testing the contact-action effects between rotating and stationary structural elements of flow-related engines, such as turbine power plants, is formed of a motor driven rotary supporting arrangement for a rotational test element and a support frame for mounting a stationary test element so that the contact-action effects between the rotational test element and the stationary test element can be evaluated. The support frame for mounting the stationary test element includes positioning devices for adjusting the position of the stationary test element which is mounted on the support frame by way of a mounting block that is suspended by spring rods which are fastened to a yoke-forming portion of the support frame. Furthermore, according to the preferred embodiment, the mounting block is connected to the yoke in a horizontal plane which passes through the axis of rotation of the rotary supporting frame by connecting members, each of which include an elongation measuring strip instrument for radial or axial force measurement, respectively, and which are connected to the mounting block by means of a ball joint.

17 Claims, 3 Drawing Figures

DEVICE FOR TESTING OF CONTACT ACTION BETWEEN ROTATING AND STATIONARY STRUCTURAL ELEMENTS OF FLOW RELATED ENGINES, ESPECIALLY GAS TURBINE POWER PLANTS

BACKGROUND AND SUMMARY OF THE INVENTION

The invention relates to a device for the testing of contact-action (rubbing) between rotating and stationary structural elements of flow-related engines especially gas turbine power plants.

With flow-related engines, for example, gas turbine power plants, problems arise regarding the selection of suitable materials for sealing elements which cooperate with each other during operation, for example, between the compressor or turbine rotor and the compressor or turbine stator, respectively.

Additionally, it is often customary for modern gas turbine power plants to provide so-called "inner-ringless" guide grids, for example, for the compressor stator with respect to "cover-bandless" rotating blades for compressors or turbine rotors.

In order to obtain a smallest possible leakage gap, it is hereby provided, to let the blade tips, in a first starting phase of the driving mechanism, brush along the run-in overlay arranged at the blade ends so that they can wear themselves in.

Furthermore, with gas turbine power plants it also must be considered that, especially in the turbine-side area, thermally caused eccentricities occuring between the rotor and stator will lead to undesirable contact-action (rubbing) for example, between the turbine rotating blade tips and the sealing surfaces at the turbine stator facing them which include a blade cover band which is constructed as a labyrinth seal.

In this and similar cases, it is important to create a material-pairing between the rotating and stationary structural elements which completely satisfy the operational requirements such as temperature loadability, deformability, and stressing and expansion behavior as well as, among other things, the adhesive ability, for example, at the sealing support or the housing.

Thus, in order to insure safe operation of a flow-related engine, especially a gas turbine power plant, it is particularly important to have the required information with respect to the above-noted properties to enable the proper selection of suitable materials within the framework of the above-noted problem at the time of designing or even during preliminary designing of such engines. To enable the proper selection, naturally requires the testing of materials or material compositions which have not previously been used in practice as well as previously utilized materials which will be utilized in a different manner within the framework of a re-design.

Therefore, the present invention has for an object, the creation of a device which is suitable for evaluating the optimal material combinations and particularly with regard to contact-action (rubbing) conditions which would occur in practice with flow-related engines such as gas turbine power plants.

To achieve this object, the testing of the rubbing effects is accomplished through measuring the relationship between rotating and stationary structural elements and/or material specimens thereof by a motor-driven body of rotation, for example, according to a preferred embodiment, a disk as well as a mounting arrangement adjustable in an axial and radial direction in relation to the disk and to which structural elements or material specimens may be mounted.

These and further objects, features and advantages of the present invention will become more obvious from the following description when taken in connection with the accompanying drawings which show for purposes of illustration only, a single embodiment in accordance with the present invention.

DETAILED DESCRIPTION OF THE INVENTION

Figure 1:
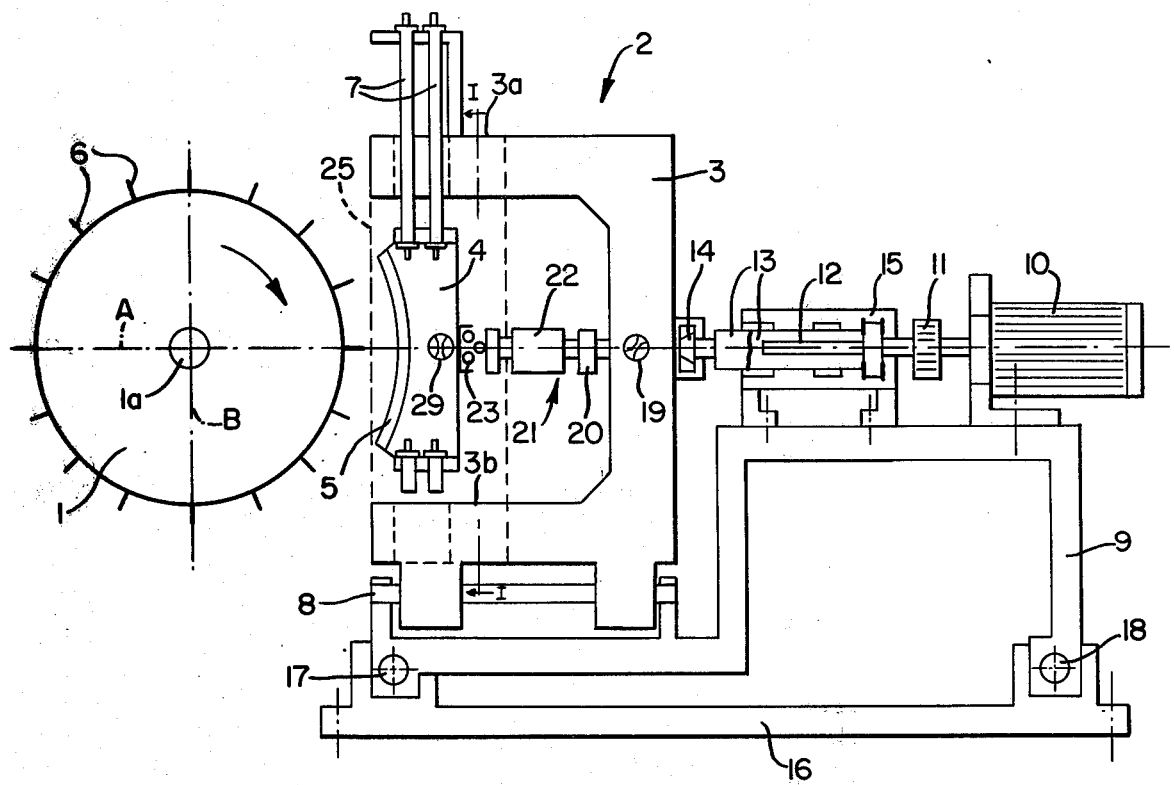
FIG. 1 illustrates schematically a frontal view of a preferred embodiment of the invention.

In the device according to FIG. 1, a disk 1 is shown cooperating with a mounting arrangement 2 which is adjustable in axial and radial directions in relation to the disk 1 so as to enable it to be aligned with the disk. The disk 1 is mounted upon a shaft 1a of a stepless variable speed drive motor which advantageously includes a torque indicator and since such motor drives are known per se, further illustration of the motor drive has been eliminated for the sake of simplifying the drawings.

The adjustable mounting 2 is constructed in the form of a U-shaped yoke 3 the two free shanks 3a, 3b of which open toward the disk 1. A mounting block 4 is springly suspended from the shank 3a so as to face the disk 1 for rotationally-symmetrically presenting a structural element or material specimen to be tested. This material specimen 5 may be, for example, a friction lining to be fastened to the flow-related engine housing and can coact with the material specimens 6 which are mounted to the disk 1 and may, for example, be rotating blade simulators.

It is also contemplated that simulated compressor or turbine guide vanes could be arranged on the mounting block 4, instead of a friction lining 5 with a starting lining disposed upon the outer circumference of the disk 1. Likewise, the contact-action of labyrinth seals at stationary seal supports can be tested by fastening the seal combs upon the disk 1 while the run-in lining of the seal carrier is fastened to the mounting block 4 opposite the seal combs.

Naturally, the present invention also encompasses the testing of actual production elements such as guide or rotating blades, in place of such simulated structural elements.

Returning to the description of the preferred embodiment illustrated in FIG. 1, it can be seen that the moutning block 4 is suspended from the yoke 3 by being fastened to spring rods 7. The spring rods 7 are arranged to extend essentially parallel to the vertical longitudinal plane of disk 1 and permit only radial and axial movements with respect to the disk.

As can be further seen from the drawings, the U-shaped yoke 3 is movable for radial adjustment in relation to the disk 1 along gliding guides 8, which may be constructed as rods, and which are arranged at an upper receiving frame 9 upon which the driving mechanism including motor 10, gearing 11 and adjusting spindle 12 are mounted so as to engage the yoke rearwardly through a pressure member 14. The threaded muff 13 is further supported at a support member 15 at the upper receiving frame 9.

For axial adjustment of the position of the yoke 3 in relation to the disk 1, the upper receiving frame 9, together with the yoke 3, may be moved along gliding guides 17, 18 which are arranged on the lower receiving frame 16 and extend parallel to the drive shaft 1a.

It should be appreciated that in the same manner that a motor 10, gearing 11, etc. is utilized to shift the yoke along the gliding guides 8, a similar drive arrangement is provided (but not shown) which engages at the side of the yoke 3 at a point 19 located in the horizontal central plane B of disk 1 for producing axial adjustment of the support arrangement 2 by shifting the yoke 3 and upper receiving frame 9 along the gliding guides 17, 18. Furthermore, the driving motors for both of these positioning drives can desirably be so-called "step-shift-motors" and the gearing such as 11 between the motor 10 and the spindle 12 may be constructed as either a chain or a wheel drive.

Turning now to the further details with respect to the mounting block 4, it can be seen from the drawings that the mounting block 4 is supported on the side facing away from disk 1 by a connecting member 21 which is positioned essentially in the horizontal longitudinal central plane A of the disk 1 and extends from the yoke 3 into contact with the rear of the mounting block 4. The connecting member 21 is adjustable by way of a pretensioned screw 20 which is connected with an elongation measuring strip instrument 22, which measures the radial force component of the contact-action between the structural elements 5 and 6, and is pivotally arranged at the mounting block 4 through a ball joint 23.

Figure 2:
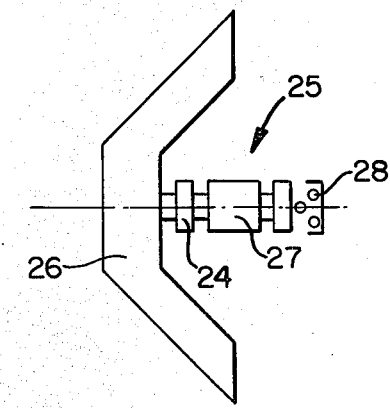
FIG. 2 shows a side view of a U-shaped yoke forming a part of the device according to FIG. 1.
Figure 3:
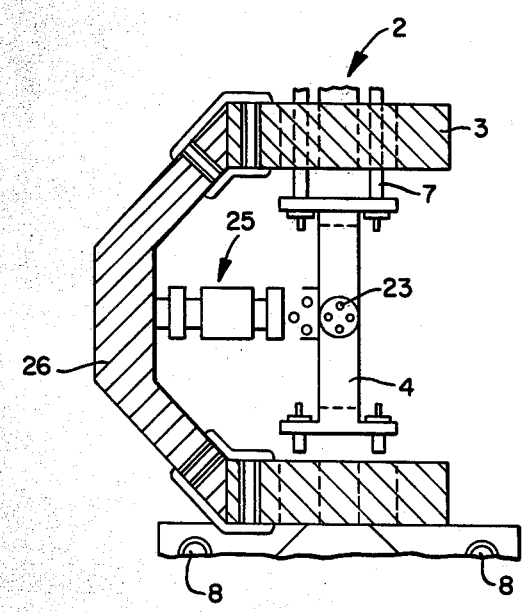
FIG. 3 is a cross-sectional view of the FIG. 1 embodiment taken along line I—I therein.

As shown in FIG. 2, a further connecting member 25 which is adjustable by way of a prestressed screw 24 and includes an elongation measuring strip instrument 27 for measuring the axial force component of the contact-action between the structural elements 5 and 6 extends from a lateral wall portion 26 of the U-shaped yoke 3. This connecting member 25 swingably engages mounting block 4 by way of a ball joint 28 at a contact point 29 (see FIG. 1).

As previously noted, the disk 1 is rotated by a stepless, variable speed drive upon the shaft 1a of which the disk is mounted, and by inclusion in the drive arrangement of a torque measuring device between the motor and the disk a determination of the friction loads can be obtained simultaneously with the determination of the radial and axial force components by the elongation measuring instruments, 22, 27. It is noted that these measuring instruments are known per se and a suitable measuring instrument for this purpose is disclosed in the brochure "Elektrisches Messen Mechanischer GröBen" edited by Hottinger Baldwin Messtechnik GMBH, 6100 Darmstadt, West-Germany. The elongation measuring instruments 22, 27 for measurement of the radial and axial forces, respectively, are calibrated by using a calibration box by way of which a statically induced force may be observed and with respect to which the measured value results can be compared.

Furthermore, the temperature profile which occurs during the rubbing produced in the contact-action test may be determined by the provision of thermo-sensitive elements in the material specimens, such as thermo-couple temperature transducers.

With the above-noted discussions of the structural aspects of the present invention in mind, the manner in which the present invention is utilized to measure the effects of the contact-action between the specimens 5 and 6, and how the obtained can be utilized to evaluate the material tested will be described.

After mounting of the structural element specimens to be tested upon the rotary support disk 1 and mounting block 4, respectively, the disk 1 and specimen thereon is caused to rotate relative to the mounting block 4. By appropriate shifting of the yoke 3 along the sliding guides 8, 17, 18 the rotating specimen 6 is brought into rubbing contact with the specimen 5 on the mounting block 4. The strain gauges or other load measuring instruments 22, 27 are the monitored in any desired form such as by a conventional uv recorder, oscilloscope, etc. to provide data on the radial and axial loads, respectively, experienced by the specimens. Likewise the torque load on the motor driving shaft 1a may be suitable monitored so as to provide other data relating to the friction load.

Accordingly, since the test apparatus of the present invention can be operated under the various service-like conditions which exist in a particular engine, by comparing the wear experienced by the specimens with the data produced by test apparatus relating to the operating load conditions, the suitability of the particular structural elements or material specimens can be properly evaluated.

Therefore, it is plain that the test apparatus disclosed herein provides a valuable method by which data representative of the evaluation criteria can be obtained under engine conditions for the purpose of evaluating the specimens tested and designing or redesigning flow-related engines, such as gas turbines, which will then be safe and durable.

While we have shown and described one embodiment in accordance with the present invention, it is understood that the same is not limited thereto but is susceptible of numerous changes and modifications as known to those skilled in the art and we therefore do not wish to be limited to the details shown and described herein but intend to cover all such changes and modifications as are encompassed by the scope of the appended claims.

We claim:

1. A device for testing the contact-action effects between rotating and stationary structural elements of flow-related engines, such as turbine power plants, comprising a motor driven rotary means for supporting a rotational test element, a support frame means for mounting a stationary test element, positioning means for adjusting the position of said stationary test element mounted on said support frame means relative to the rotational test element supported by said rotary means in radial as well as axial directions, and measuring means for evidencing the effects of contact-action between the rotational and stationary test elements, wherein the support frame means is a U-shaped yoke having two free shanks opening toward the rotary means and is provided with a springly-suspended mounting block, said mounting block having a mounting surface facing said rotary means for mounting a specimen structural element to be tested.

2. A device according to claim 1, wherein the mounting block is suspended by being fastened to spring rods which are connected to said yoke above said mounting block so as to extend essentially parallel to the vertical longitudinal plane of the rotary means.

3. A device according to claim 2, wherein the positioning means includes gliding guides along which said U-shaped yoke is displaceable for radial adjustment of the yoke with respect to said rotary means and a driving mechanism for displacing said yoke upon said guides.

4. A device according to claim 3, wherein the U-shaped yoke is carried by an upper receiver frame along said gliding guides, and wherein said guides are associated with a lower receiver frame which extends parallel to the axis of rotation of a specimen supporting disk of said rotary means.

5. A device according to claim 4, wherein said positioning means also includes driving means on the lower receiver frame for providing axial adjustment of the mounting block with respect to the supporting disk.

6. A device according to claim 4, wherein the mounting block is supported at its side away from said supporting disk, in the horizontal longitudinal plane of the disk, by a connecting member which is adjustable radially with respect to the disk by a prestressed screw, said connecting member comprising an elongation measuring strip instrument for radial force measurement and being connected to said mounting block by means of a ball joint.

7. A device according to claim 6, wherein lateral support for said mounting block is provided by a further connecting member which is adjustable, axially with respect to the supporting disk in the horizontal longitudinal plane of the disk, by prestressed screw means, said further connecting member comprising an elongation measuring strip instrument for axial force measurement and being connected to said mounting block by means of a ball joint.

8. A device according to claim 7, wherein the drive of said motor driven rotary means is provided with a torque measuring device for determination of occurring cutting and friction loads.

9. A device according to claim 1, wherein the positioning means includes gliding guides along which said U-shaped yoke is displaced for radial adjustment of the yoke with respect to said rotary means and a driving mechanism for displacing said yoke upon said guides.

10. A device according to claim 9, wherein the U-shaped yoke is carried by an upper receiver frame along said gliding guides, and wherein said guides are associated with a lower receiver frame which extends parallel to the axis of rotation of a speciment supporting disk of said rotary means.

11. A device according to claim 10, wherein said positioning means also includes driving means on the lower receiver frame for providing axial adjustment of the mounting block with respect to the supporting disk.

12. A device according to claim 11, wherein the mounting block is supported at its side away from said supporting disk, in the horizontal longitudinal plane of the disk, by a connecting member which is adjustable radially with respect to the disk by a prestressed screw, said connecting member comprising an elongation measuring strip instrument for radial force measurement and being connected to said mounting block by means of a ball joint.

13. A device according to claim 12, wherein lateral support for said mounting block is provided by a further connecting member which is adjustable, axially with respect to the supporting disk in the horizontal longitudinal plane of the disk, by prestressed screw means, said further connecting member comprising an elongation measuring strip instrument for axial force measurement and being connected to said mounting block by means of a ball joint.

14. A device according to claim 13, wherein the drive of said motor driven rotary means is provided with a torque measuring device for determination of occurring cutting and friction loads.

15. A device accordings to claims 8 or 14, wherein said drive for said rotary means includes a stepless variable speed motor.

16. A device according to claims 1 or 5 or 8 or 14, wherein said yoke is controllable to be simultaneously and independently displaceable with said mounting block in axial and radial directions with respect to said rotational test element.

17. A device according to claim 15, wherein said yoke is controllable to be simultaneously and independently displaceable with said mounting block in axial and radial directions with respect to said rotational test element.

* * * * *